US006284455B1

(12) United States Patent
Hsu et al.

(10) Patent No.: US 6,284,455 B1
(45) Date of Patent: Sep. 4, 2001

(54) **DIAGNOSIS OF *PENAEUS MONODON*-TYPE BACULOVIRUS BY PCR**

(75) Inventors: Ya-Li Hsu, Taipei; Todd Hsu, Keelung, both of (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/352,996

(22) Filed: Jul. 13, 1999

(51) Int. Cl.$^7$ ................................ C12Q 1/70; C12P 19/34
(52) U.S. Cl. ........................ 435/5; 435/91.1; 435/91.2; 424/204.1; 536/23.72
(58) Field of Search .................... 435/5, 91.1, 91.2; 424/204.1; 536/23.72

(56) References Cited

U.S. PATENT DOCUMENTS 5,824,535    10/1998    Kou et al. .

OTHER PUBLICATIONS

Belcher et al. Journal of Virological Methods, 1998, vol. 74, pp. 21–29, Sep. 1998.*

Destoumieus, et al., "Penaeidins, a New Family of Antimicrobial Peptides Isolated from the Shrimp *Penaeus vannamei* (Decapoda)", Journal of Biological Chemistry, vol. 272, No. 15, pp. 28398–28406, Nov. 7, 1997.

Bonami, et al., "Purification and Characterization of the infectious hypodermal and haematopoietic necrosis virus of penaeid shrimps", Journal of General Virology, vol. 71, pp. 2657–2664, 1990.

Bjornson, et al., Characterization of the nucleotide sequence of the *Lymantria dispar* nuclear polyhedrosis virus DNA polymerase gene region:, vol. 73, pp. 3177–3183, 1992.

Chang, et al., "Purification and Amplification of DNA from *Penaeus Monodon*–Type Baculovirus (MBV)", Journal of Invertebrate Pathology, vol. 62, pp. 116–120, 1993.

Wang, et al., "Purification and genomic analysis of baculovirus associated with white spot syndrome (WSBV) of *Penaeus mondon*", vol. 23 pp. 239–242, Nov. 23, 1995.

* cited by examiner

*Primary Examiner*—Ali R. Salimi
(74) *Attorney, Agent, or Firm*—Fei-Fei Chao; Venable, Baetjer, Howard & Civiletti, LLP

(57) ABSTRACT

This invention relates to the methods of detecting Penaeus monodon baculovirus (MBV). Two methods are established: the first one is a polymerase chain reaction (PCR) and the second one is an ELISA. For the PCR method, two sets of primers are designed. The first set of primers is designed from the conserved sequences of nuclear polyhedrosis viruses (NPVs) DNA polymerase genes. The second set of primers is designed from the genomic DNA of MBV. The antibody for ELISA is an antiserum against the occlusion bodies of MBV.

3 Claims, 8 Drawing Sheets

Figure 1:
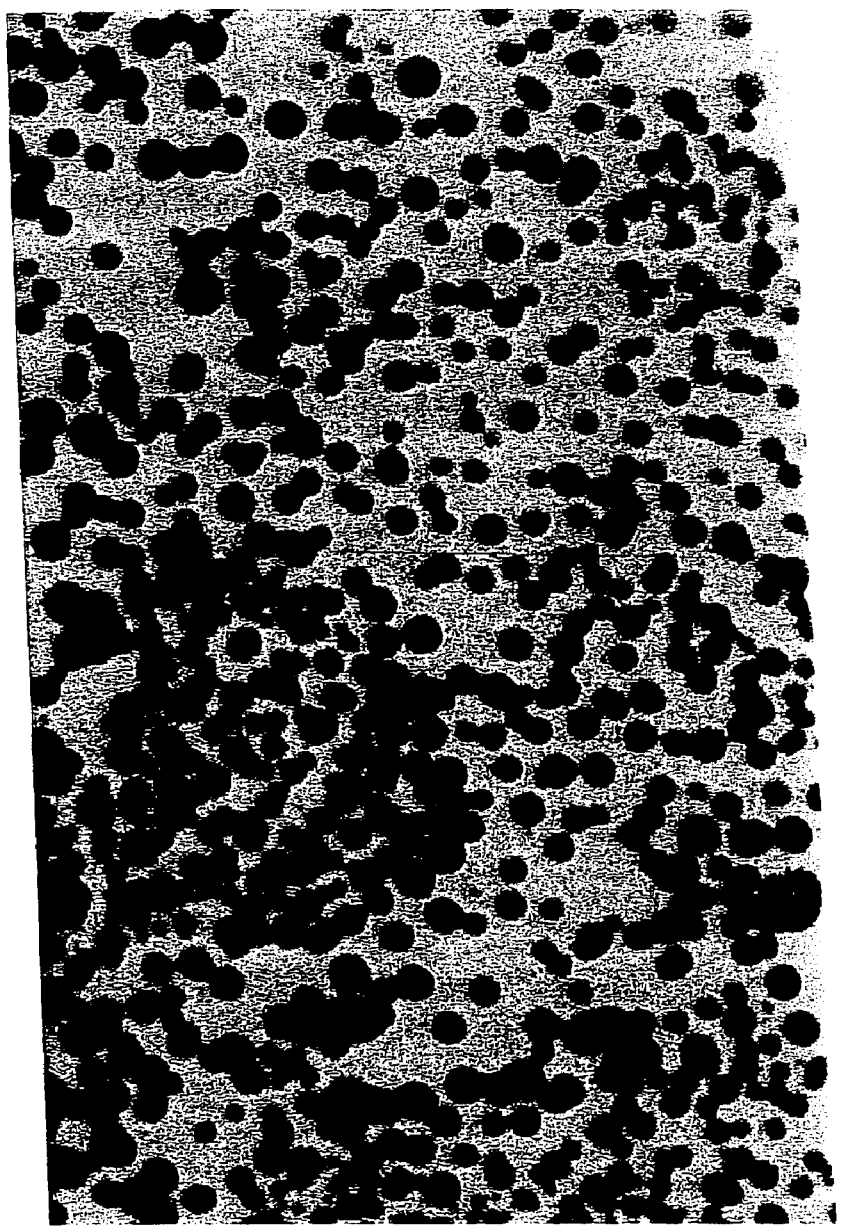

```
                                  primer 1 ⟶
TCTAGAGTGA ATCGCGTGCA CATGCAGACG TAGCAGACCA TTATCCACAA    50

ACACACAAGT CAGCTGATCG CCAATGGCTT TGTGCAATAG TGCTGCAACG   100
    PA1 primer ⟶
ACTGGACTGT CCACGCCGCC CGATAGTCCG AGCAATACTT GCTTGTCACC   150

GATTTGTCTC TTTGGACTGC GCAATACGCA TATCAGCGAT ATTGTCTGGA   200

GTCCACTCAC CAGCACAATC GCAAATCTGA TGGACAAAAC GACCTAGCAG   250

CGCTTGACCT TGTAGGGTGT GCGTCACTTC AGGATGGAAC TGTAGACCGT   300

AGTATTGCTT GTCATCATAT GCCATTATCG CAATCGGGCA GCTTGGCGCA   350

TCAGCAACGA TGTCAATGCC TTCAGGCGCT TCGATGGCTT TATCACAATG   400

GCTCATCCAA ACGTTTAGCT TGGCAGCCGG GCCGTCAGTC TTGCTGTCTT   450

CGATACCGTC AGTCAGCTGC GAGTGACCAT TTACTTCGAT GGTCGCCGCA   500

CCAAACTCAT GAATATCACT GGCATAACCT GCCCGCCAAA ACGATCTGCC   550
                                      ⟵ PA2 primer
ATCGCCTGCA TACCGTAGCA AATACCCAAT ACAGGCACGC CTAGGATCAA   600

ACACCGCGTC ATTAGTACGC GGGCTGTTAT CTGCATGTGC ACGCGATTCA   650
                                              ⟵ primer 2
CTCTAGATCT AGAGTGAATC GCGTGCACTG GCAGATCTTC TACTACATTC   700

ACATCGATTC TAGA                                          714
```

Fig. 4

(A)

5'-AGTGCTGCAACGACTGGACTGTCC-3' PA1
5'-TGATCCTAGGCGTGCCTGTATTGGG-3' PA2

(B)

SEQUENCE LISTING

```
<160> NUMBER OF SEQ ID NOS:  8

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer for PCR

<400> SEQUENCE: 1
caatctactt tccgctgtct ac                                                22

<210> SEQ ID NO 2
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      Primer for PCR

<400> SEQUENCE: 2
gtagacagcg gaaagtagat tg                                               22

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer for PCR

<400> SEQUENCE: 3
aattcgaacg agctgagcca gcag                                             24

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer for PCR

<400> SEQUENCE: 4
agttcgaagg caagctttat tgaggc                                           26

<210> SEQ ID NO 5
<211> LENGTH: 714
<212> TYPE: DNA
<213> ORGANISM: Nuclear Polyhedrosis Virus
<220> FEATURE:
<223> OTHER INFORMATION: Description of Sequence: PCR Fragment

<400> SEQUENCE: 5
tctagagtga atcgcgtgca catgcagacg tagcagacca ttatccacaa acacacaagt        60
cagctgatcg ccaatggctt tgtgcaatag tgctgcaacg actggactgt ccacgccgcc       120
cgatagtccg agcaatactt gcttgtcacc gatttgtctc tttggactgc gcaatacgca       180
tatcagcgat attgtctgga gtccactcac cagcacaatc gcaaatctga tggacaaaac       240
gacctagcag cgcttgacct tgtagggtgt gcgtcacttc aggatggaac tgtagaccgt       300
agtattgctt gtcatcatat gccattatcg caatcgggca gcttggcgca tcagcaacga       360
tgtcaatgcc ttcaggcgct tcgatggctt tatcacaatg gctcatccaa acgtttagct       420
tggcagccgg gccgtcagtc ttgctgtctt cgataccgtc agtcagctgc gagtgaccat       480
ttacttcgat ggtcgccgca ccaaactcat gaatatcact ggcataacct gcccgccaaa       540
acgatctgcc atcgcctgca taccgtagca aatacccaat acaggcacgc ctaggatcaa       600
acaccgcgtc attagtacgc gggctgttat ctgcatgtgc acgcgattca ctctagatct       660
agagtgaatc gcgtgcactg gcagatcttc tactacattc acatcgattc taga            714

<210> SEQ ID NO 6
<211> LENGTH: 511
<212> TYPE: DNA
<213> ORGANISM: Nuclear Polyhedrosis Virus
<220> FEATURE:
<223> OTHER INFORMATION: Description of Sequence: PCR Fragment

<400> SEQUENCE: 6
```

```
agtgctgcaa cgactggact gtccacgccg cccgatagtc cgagcaatac ttgcttgtca      60
ccgatttgtc tctttggact gcgcaatacg catatcagcg atattgtctg gagtccactc     120
accagcacaa tcgcaaatct gatggacaaa acgacctagc agcgcttgac cttgtagggt     180
gtgcgtcact tcaggatgga actgtagacc gtagtattgc ttgtcatcat atgccattat     240
cgcaatcggg cagcttggcg catcagcaac gatgtcaatg ccttcaggcg cttcgatggc     300
tttatcacaa tggctcatcc aaacgtttag cttggcagcc gggccgtcag tcttgctgtc     360
ttcgataccg tcagtcagct gcgagtgacc atttacttcg atggtcgccg caccaaactc     420
atgaatatca ctggcataac ctgcccgcca aaacgatctg ccatcgcctg cataccgtag     480 caaatacccca atacaggcac gcctaggatc a                                    511
```

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer for PCR ("n" stands for inosine)

<400> SEQUENCE: 7

```
tctagagtna atcgcgtnca catgcana                                         28
```

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer for PCR ("n" stands for inosine)

<400> SEQUENCE: 8

```
tctagaatcn atgtgaatgt anta                                             24
```

DIAGNOSIS OF *PENAEUS MONODON*-TYPE BACULOVIRUS BY PCR

I. FIELD OF THE INVENTION

The present invention relates to a method for detecting occluded baculovirus, more specially, Penaeus monodon baculovirus (MBV), using polymerase chain reaction (PCR). Two pairs of primers are designed, the first pair of primers (i.e., SEQ ID NO:1 and SEQ ID NO:2) are occluded baculovirus (particularly nuclear polyhedrosis virus [NPV]) specific, which can detect baculovirus that produces polyhedra occlusion bodies. The second pair of primers (i.e., SEQ ID NO:3 and SEQ ID NO:4) are MBV specific, which can detect MBV exclusively. The present invention also relates to an enzyme-linked immunosorbent assay (ELISA) method for detecting MBV occlusion bodies.

II. BACKGROUND OF THE INVENTION

Since the technological development in artificial fertilization, mass seed production, and feed formulation for cultured crustaceans, cultured shrimp (especially penaeid shrimp) has become number one cultivated crustacean in Southeast Asia, especially in Taiwan. In recent years, there have been numerous reports regarding disease outbreaks which cause substantial losses in shrimp production in Taiwan and southeast Asia. Pathogens, such as bacteria, viruses, and fungi, along with environmental stressors such as temperature fluctuation, heavy rainfall, overfeeding, and industrial and agricultural pollutants, are considered to be the major contributors for the outbreaks. Among these, viral infections are particularly of concern, primarily because viral diseases cannot be cured by therapeutic reagents and an early and sensitive detection of the disease is the most effective means for containment.

To date, nearly twenty penaeid shrimp viral diseases have been discovered. Among them, six major viruses were found, in which four baculoviruses, namely Penaeus monodon baculovirus (MBV), baculoviral midgut necrosis virus (BMN), baculovirus penaei (BP), and white spot syndrome virus (WSSV), are the most important ones due to their wide distribution and causes of high mortality in penaeid shrimp.

Baculoviruses are a large group of viruses which infect only arthropods. There are three subgroups of baculovirus, namely nuclear polyhedrosis viruses (NPV), granulosis viruses (GV), and non-occluded baculoviruses. NPV and GV are occluded forms of baculoviruses. The virions (enveloped nucleocapsids) in NPV and GV are embedded in a crystalline protein matrix, which is referred to as an inclusion or occlusion body. The occlusion body is found responsible for spreading the infection between organisms. The characteristic feature of the NPVs is that many virions are embedded in each occlusion body. The NPV occlusion bodies are relatively large (up to 5 micrometers). Occlusion bodies of the GV viruses are smaller and contain a single virion each. The crystalline protein matrix of the occlusion bodies of both forms is primarily composed of a single 25,000 to 33,000 dalton polypeptide which is known as polyhedrin or granulin. Baculoviruses of the non-occluded subgroup do not produce a polyhedrin or granulin protein, and do not form occlusion bodies.

In nature, baculovirus infection is initiated when an arthropod ingests food contaminated with baculovirus particles, typically in the form of occlusion bodies for an NPV. The occlusion bodies dissociate under the alkaline conditions of the midgut, releasing individual virus particles which then invade epithelial cells lining the gut.

Within a host cell, the baculovirus migrates to the nucleus where replication takes place. Initially, certain specific viral proteins (such as DNA polymerase) are produced within the infected cell via the transcription and translation of so-called "early genes". These proteins are required for the replication of the viral DNA. The infected cell later produces large amounts of "late viral gene products", which include components of the nucleocapsid which surrounds the viral DNA during the formation of progeny virus particles. The progeny virus particles then migrate to the cell membrane where they acquire an envelope as they bud out from the surface of the cell. This non-occluded virus can then infect other cells.

Polyhedrin synthesis begins late in the post-infection period. At that time, there is a decrease in the number of budded virus particles, and progeny virus particles are then embedded in occlusion bodies. Occlusion body formation continues until the cell dies or lyses, thereby releasing the occlusion bodies which can then spread the infection to other host cells.

Among shrimp baculoviruses, MBV and BP are NPVs, which are characterized by the existence of occlusion bodies and polyhedrin. Insect baculoviruses, AcMNPV, BmSNPV, LdMNPV and OpMNPV, also belong to NPVs. Among insect baculoviruses, AcMNPV (Autographa californica nuclear polyhedrosis virus) has been extensively studied. ACMNPV has a genome of 130 kbps of doublestranded, circular DNA. It belongs to the family Baculoviridae, subfamily Eubaculo-virinae, genus Nuclear Polyhedrosis Virus (NPV), and the subgenus Multiple Nucleocapsid Virus, which are characterized by the formation of viral occlusion bodies or polyhedra in the nuclei of infected host cells. DNA sequencing within the genome of AcMNPV is well documented.

Recently, Kuo et al. (U.S. Pat. No. 5,824,535) has reported the identification, purification, and detection of WSSV, a baculovirus associated with white spot syndrome. However, WSSV is a non-occluded baculovirus, which can not be used to detect occluded baculovirus.

In 1993, Chang et al., *J. Invertebr. Pathol.*, 62:116–120, disclosed a PCR method using polyhedrin gene to detect MBV. However, polyhedrin exists in all NPVs, which includes not only occluded insect baculoviruses (such as ACMNPV, BmSNPV, LdMNPV, and OpMNPV), but also shrimp viruses such as BP and MBV. In addition, according to a report by Bjornson et al. (Bjornson et. al., *J. General Virol.*, 73:3177–3183), there is a 80% sequence homology in polyhedrin genes among NPVs. Therefore, using a pair of primers derived from the DNA sequences of insect polyhderin genes for PCR, as described by Chang et al. (supra), can not sensitively and exclusively detect MBV, and the industry is still in need of a highly specific and sensitive method for the detection of MBV infection as a means of containing the disease.

III. SUMMARY OF THE INVENTION

The first embodiment of the present invention provides a method for detecting occluded baculoviruses using polymerase chain reaction (PCR). Two pairs of primers are designed. The first pair of primers is originated from the conserved sequences of the DNA polymerase genes of nuclear polyhedrosis viruses (NPVs). This pair of primers can detect occluded baculoviruses using PCR. The preferable first pair of primers (Primer 1 and Primer 2) has the DNA sequences of SEQ ID NO:7 and SEQ ID NO:8. This pair of primers are designed from the conserved sequences of the DNA polymerase genes of Autographa californica nuclear polyhedrosis virus (AcMNPV) and Lymantria dispar nuclear polyhedrosis virus (LdNNPV). The most preferable first pair of primers (P1 and P2) has the DNA sequences of SEQ ID NO:1 and SEQ ID NO:2. These two DNA sequences are derived from the DNA polymerase-like gene of MBV. When an MBV DNA template is used, both pairs of primers produce a 714-bp DNA PCR fragment (SEQ ID NO:5). When an AcMNPV DNA is used as template, both pairs of primers produce a 621-bp PCR fragment.

The second pair of primers (PA1 and PA2) (SEQ ID NO:3 and SEQ ID NO:4) is a pair of nested primers designed from the 714-bp PCR product produced by P1 and P2 using MBV DNA as template. Using this pair of nested primers, a 511-bp PCR product (SEQ ID NO:6) is produced when MBV DNA is used as template. PA1 and PA2 are specific for MBV detection because they do not produce any PCR products when DNA templates from other sources, such as a non-MBV NPV (e.g., AcMNPV), white spot syndrome virus (WSSV), or normal shrimp tissue homogenates, are used.

The PCR method comprises the following steps: (1) amplifying DNA in a sample comprising the first or second pair of primers described above by PCR to obtain an amplified product; and (2) analyzing the amplified product by electrophoresis. The preferable electrophoresis method is agarose gel electrophoresis, more preferably, a 2% agarose gel electrophoresis. The preferable annealing temperature for the first 5 cycles of PCR is 42° C.

The second embodiment of this invention provides a method for detecting MBV using enzyme-linked immunosorbent assay (ELISA). ELISA requires the interaction of two antibodies: The first antibody is against purified occlusion bodies of MBV. This antibody can be a monoclonal or polyclonal antibody, although polyclonal is preferred. The first antibody can be obtained via intraspleenic immunization. The preferable animal for producing the first antibody is rabbit, such as New Zealand rabbit. The first antibody can detect MBV occlusion bodies at nanogram levels.

The second antibody is an enzyme-linked antibody against the first antibody. When the first antibody is produced in rabbit, the second antibody can be a goat anti-rabbit IgG. When the two antibodies interact, a color reaction is developed, which can be monitored by the change of optical density. The preferable enzyme for ELISA is horseradish peroxidase, which will produce a color reaction when 3,3', 5,5'-tetramethyl benzidine is added. Such color reaction can be measured by optical density at 450 nm.

The ELISA method comprises the following steps: (1) obtaining a first antibody against MBV occlusion bodies; (2) coating the MBV occlusion bodies (i.e., the antigen) to a microtiter plate; (3) mixing the first antibody with a test sample and then adding the mixture to the microtiter plate; (5) adding an enzyme-linked second antibody to the plate; and (6) analyzing a reaction (e.g., a color development) between the first and second antibody.

IV. BRIEF DESCRIPTION OF THE DRAWINGS

FIG. 1 is a light microscopic photograph (400×) of purified occlusion bodies from monodon-type baculovirus (MBV). The occlusion bodies were stained with eosin.

Figure 2:
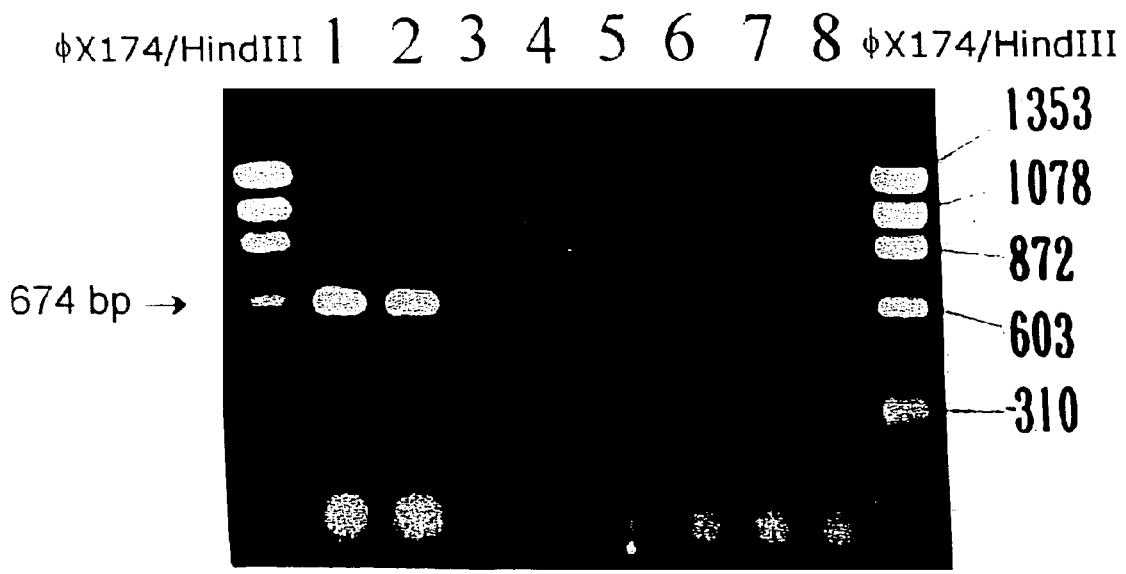

FIG. 2 is an agarose gel analysis of PCR products, which confirms that the purified occlusion bodies (as shown in FIG. 1) contain the genomic DNA of MBV. The conserved sequences of insect baculovirus polyhedrin genes were used to design PCR primers. DNA templates used were as follows: Lane 1: MBV DNA template; Lane 2: AcMNPV DNA template; Lane 3: WSSV template; Lane 4: DNA extracted from a cell line derived from the oka organ of the Penaeus monodon (PMO); Lane 5: DNA extracted from postlarval of tiger prawn; Lane 6: DNA extracted from hepatopancreatic tissue of adult tiger prawn; Lane 7: DNA extracted from intestinal tissue of adult tiger prawn; Lane 8: no DNA template. Size markers (Hind III cut of phage X174 DNA) are shown on both sides.

Figure 3:
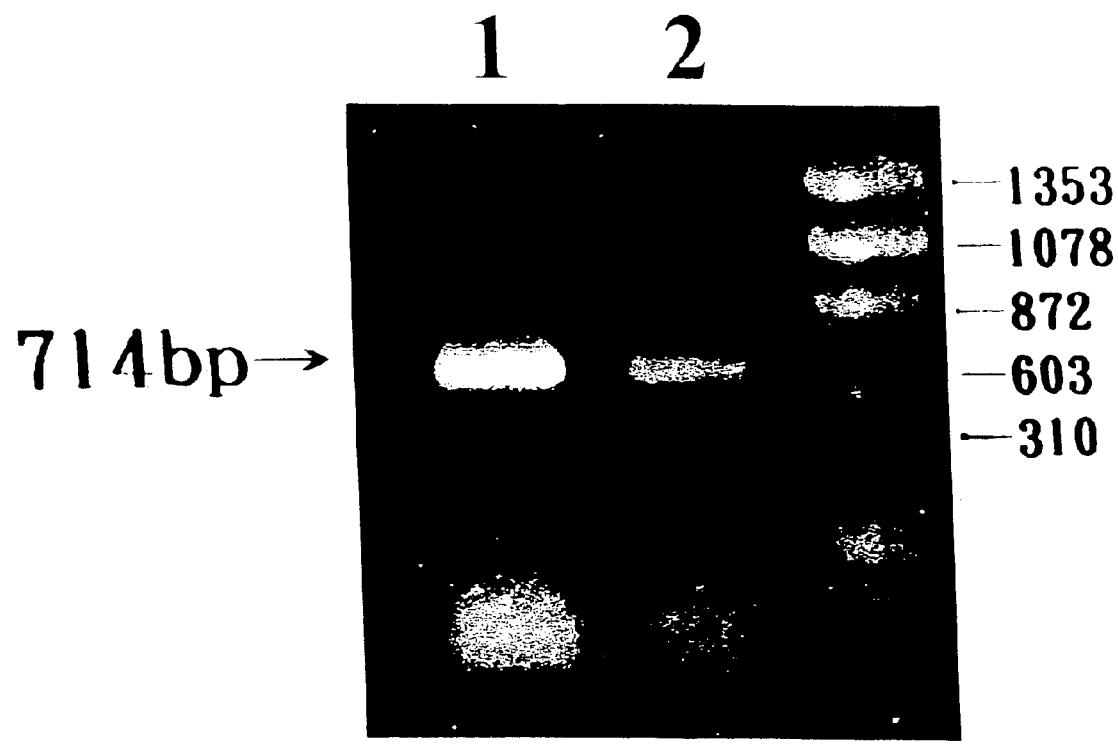

FIG. 3 shows the effect of annealing temperature on the production of PCR fragments. The primers used in this study were Primer 1 and Primer 2 (SEQ ID NO:7 and SEQ ID NO:8), which were designed from the conserved sequences of the DNA polymerase genes of Autographa californica nuclear polyhedrosis virus (AcMNPV) and Lymantria dispar nuclear polyhedrosis virus (LdMNPV). Lane 1: annealing temperature for the first 5 PCR cycles at 42° C. Lane 2: annealing temperature for the first 5 PCR cycles at 45° C.

FIG. 4 is the DNA sequence of the 714-bp PCR product produced by Primer 1 and Primer 2 (SEQ ID NO:7 and SEQ ID NO:8) when MBV DNA template was used for PCR amplification. Primers P1 and P2 (SEQ ID NO:1 and SEQ ID NO:2) are shown in rectangular boxes, which are part of the genomic DNA of the MBV. The DNA sequence of the 714-bp PCR product produced by P1 and P2 when MBV DNA template was used were identical to that produced by Primer 1 and Primer 2. TAG stop codons are underlined. The nested primers (SEQ ID NO:3 and SEQ ID NO:4) are shown as PA1 and PA2 primers. PA1 and PA2 are also part of the genomic DNA of the MBV.

Figure 5:
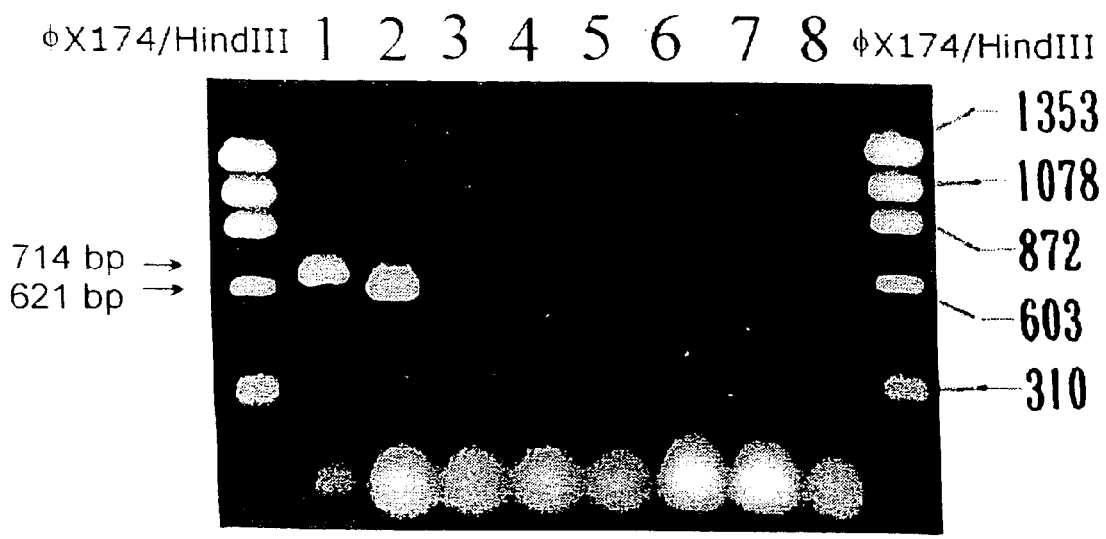

FIG. 5 is the agarose gel analysis of PCR products using P1 and P2 (SEQ ID NO:1 and SEQ ID NO:2). Lane 1: MBV DNA template; Lane 2: ACMNPV DNA template; Lane 3: WSSV DNA template; Lane 4: DNA extracted from the PMO cell line (derived from the oka organ of the Penaeus monodon); Lane 5: DNA extracted from postlarval of tiger prawn; Lane 6: DNA extracted from hepatopancreatic tissue of adult tiger prawn; Lane 7: DNA extracted from intestinal tissue of adult tiger prawn; Lane 8: no DNA template. Size markers (Hind III cut of phage X 174 DNA) are shown on both sides. A 714-bp PCR fragment was produced when MBV DNA was used as template (Lane 1). A 621-bp PCR fragment was produced when AcMNPV DNA was used as template (Lane 2).

Figure 6:
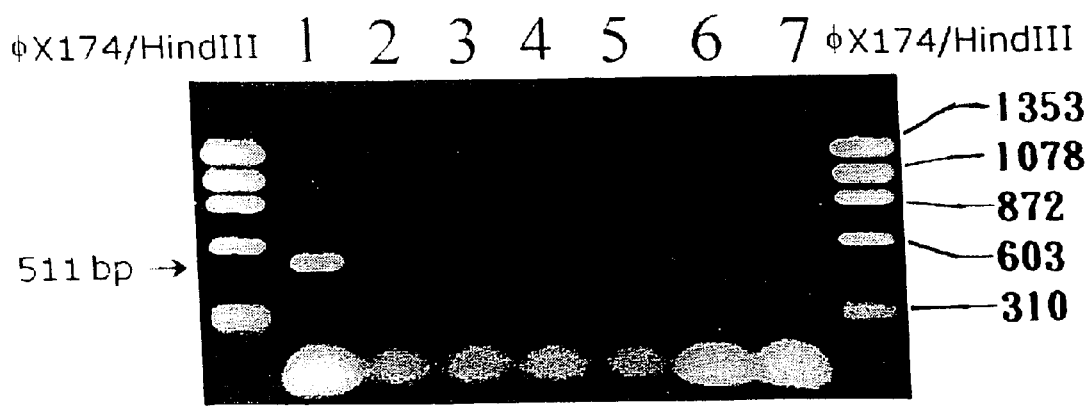

FIG. 6 is the agarose gel analysis of PCR products using PA1 and PA2 (SEQ ID NO:3 and SEQ ID NO:4) designed from the 714-bp PCR fragment (as described in FIGS. 4 and 5). (A) DNA sequences (SEQ ID NO:3 and SEQ ID NO:4) of PA1 and PA2. (B) Agarose gel electrophoresis of PCR products using the following DNA templates: Lane 1: MBV; Lane 2: AcMNPV; Lane 3: WSSV; Lane 4: PMO cells; Lane 5: postlarval of adult tiger prawn; Lane 6: hepatopancreatic tissue of adult tiger prawn; lane 7: intestinal tissue of adult tiger prawn. Size markers are shown on both sides.

Figure 7:
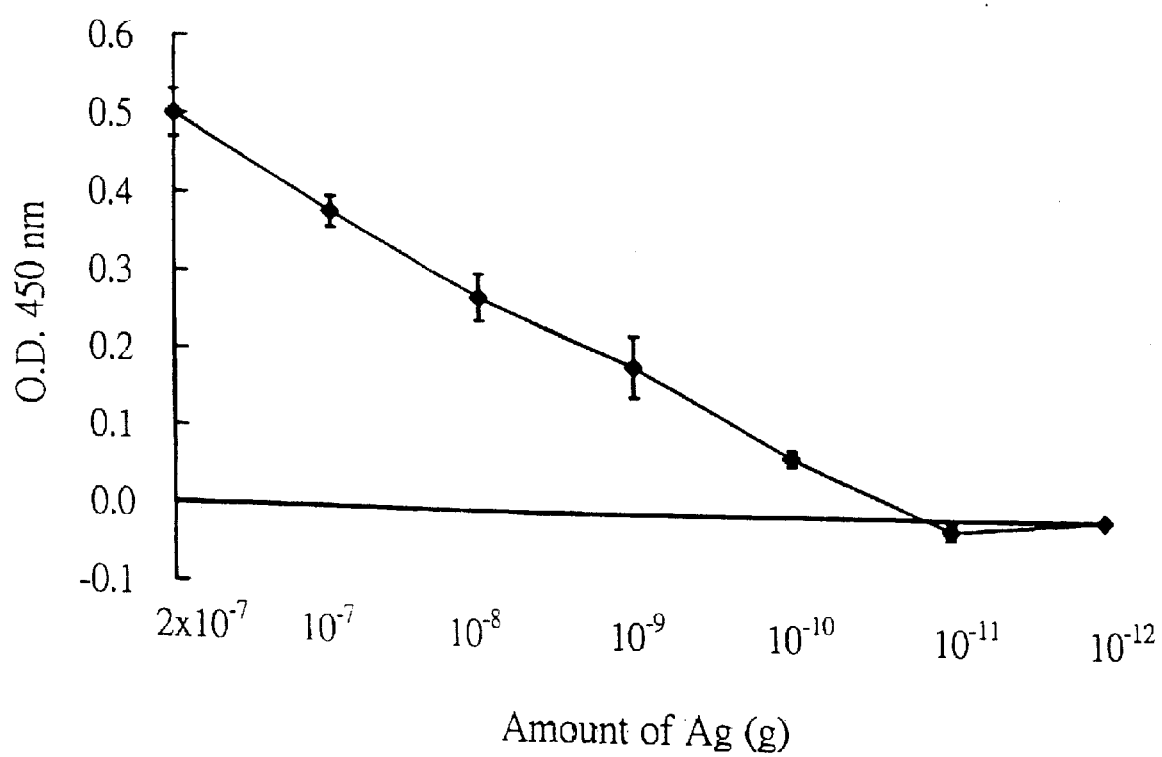

FIG. 7 is the sensitivity test of ELISA to MBV. Ten-fold dilutions of purified occlusion bodies of MBV were coated onto 96-well microtiter plates. Then, different titers of the polyclonal antibodies against MBV occlusion bodies were added to the microtiter plates, followed by the addition of goat anti-rabbit IgG-horseradish peroxidase serum, and 3,3', 5,5'-tetramethyl benzidine. The optical density of the wells in the microtiter plate were measured at 450 nm. The vertical bar represents standard deviation (S.D.) of the samples.

Figure 8:
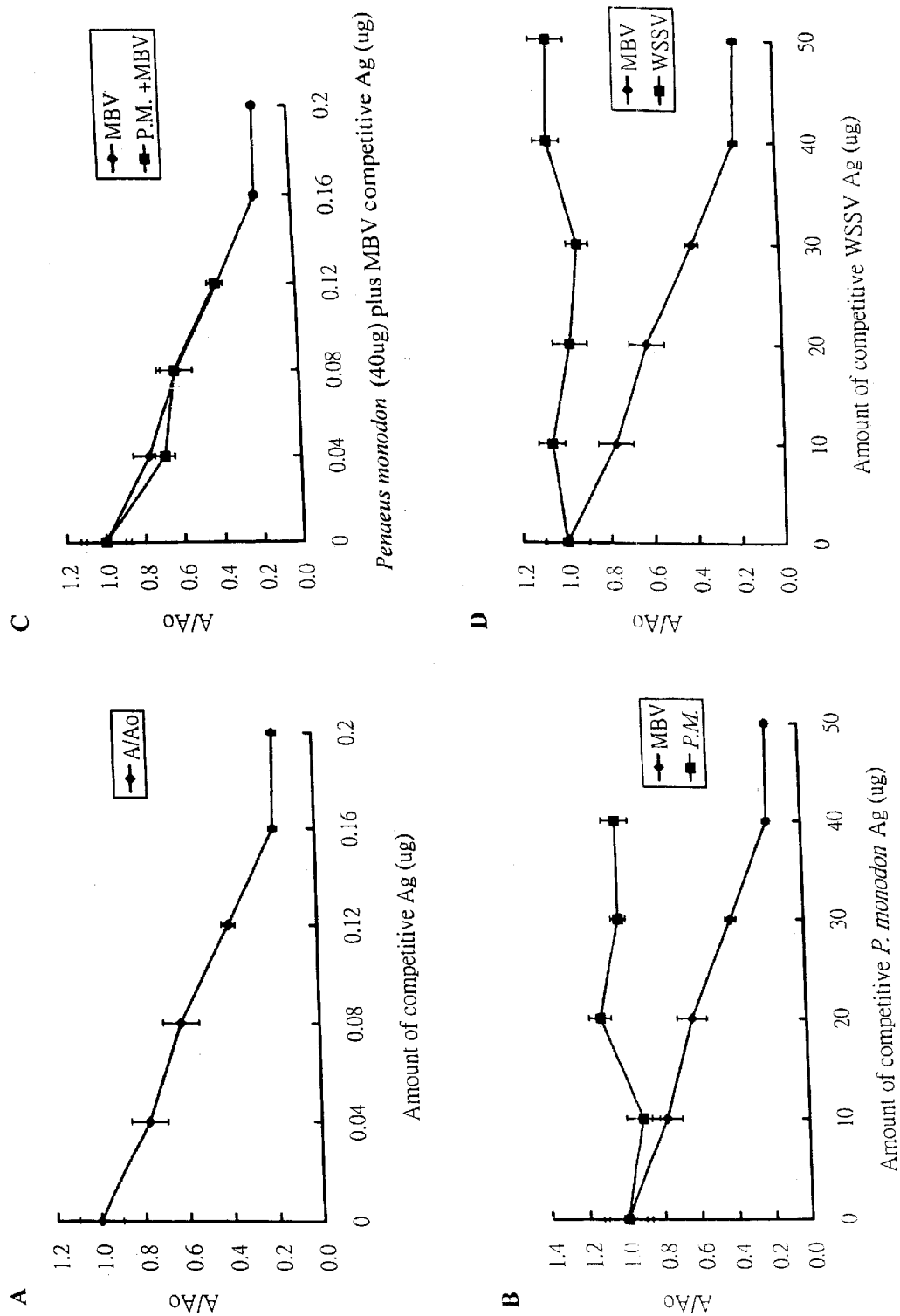

FIG. 8 shows the competitive ELISA test for MBV. (A) Standard curve for the competitive ELISA. A 1000-fold dilution of rabbit anti-MBV antiserum was mixed with different concentrations of purified occlusion bodies of MBV at 37° C. for 1 hour, then the mixture was added to MBV-coated (0.2 μg) microtiter plates and ELISA was performed. (B) Competitive ELISA for MBV and tiger prawn. A 1000-fold dilution of antibodies was mixed with different concentrations of MBV or with homogenates of the tiger prawn. (C) Competitive ELISA for MBV and MBV+ tiger prawn. Different concentrations of MBV or MBV+40 μg tissue homogenate were used as antigens. (D) Competitive ELISA for MBV and WSSV. Different concentrations of MBV and WSSV were used as antigens in the competitive ELISA.

V. DETAILED DESCRIPTION OF THE INVENTION

The first embodiment of the invention provides for a polymerase chain reaction (PCR) method to detect MBV using two pairs of primers specific to MBV genomic DNA. The first pair of primers is designed from the conserved sequences of the DNA polymerase genes of NPVs. The DNA polymerase genes share 40%–50% sequence homology among insect baculoviruses (Bjornson et al., *J. General Virol.* 73:3177–3183, supra), which are much more diverse than the polyhedrin genes of nuclear polyhedrosis viruses (NPVs) (which share a 80% sequence homology among insect baculoviruses). The PCR method using a pair of primers designed from the conserved sequences of the DNA polymerase genes is therefore more selective than that of polyhedrin genes.

P1 and P2 are the preferable first pair of primers. They are derived from the DNA polymerase gene of MBV. P1 and P2 are designed according to a pair of conserved sequences (i.e., Primer 1 and Primer 2, SEQ ID NO:7 and SEQ ID NO:8) taken out from the DNA polymerase genes of *Autographa californica* nuclear polyhedrosis virus (AcMNPV) and *Lymantria dispar* nuclear polyhedrosis virus (LdMNPV). Primer 1 and Primer 2 (SEQ ID NO:7 and SEQ ID NO:8) have the following DNA sequences:

Primer 1: 5'-TCTAGAGTIAATCGCGTICACATGCAIA-3' (SEQ ID NO:7)

Primer 2: 5'-TCTAGAATCIATGTGAATGTAITA-3' (SEQ ID NO:8)

wherein "I" stands for inosine and an Xba I recognition site (TCT AGA) is added to the 5' end of each primer.

Using Primer 1 and Primer 2, a 714-bp PCR product (SEQ ID NO:5) is generated from an MBV DNA template. This PCR fragment is sequenced (FIG. 4). This 714-bp PCR fragment is not a part of the AcMNPV or LdMNPV DNA polymerase gene. Rather, it is a part of the genomic DNA of MBV, as evident by the low homology between the 714-bp PCR fragment and the DNA polymerase genes of AcMNPV and LdMNPV.

Also, as shown in FIG. 4, the DNA sequence of the 714-bp PCR fragment show that after PCR, in the areas where Primer 1 and Primer 2 are, the "I"s (i.e., inosines) in Primer 1 and Primer 2 have changed into "G"s (guanines). Based on these findings, another first pair of primers, namely, P1 and P2 (SEQ ID NO:1 and SEQ ID NO:2), are designed. P1 and P2 have the following sequences:

P1: 5'-TCTAGAGTGAATCGCGTGCACATGCAGA-3' (SEQ ID NO:1)

P2: 5'-TCTAGAATCGATGTGAATGTAGTA-3' (SEQ ID NO:2)

As shown in FIGS. 4–5, using P1 and P2, a 714-bp PCR product (SEQ ID NO:5) is produced when an MBV DNA template is used. This 714-bp PCR product is identical to the one generated by Primer 1 and Primer 2.

The second pair of primers is a pair of nested primers, namely, PA1 and PA2 (SEQ ID NO:3 and SEQ ID NO:4), which are designed from DNA sequence analysis of the 714-bp PCR product as shown in FIG. 4. These primers have the following DNA sequences (FIG. 6(A)):

PA1: 5'-AGTGCTGCAACGACTGGACTGTCC-3' (SEQ ID NO:3)

PA2: 5'-TGATCCTAGGCGTGCCTGTATTGGG-3' (SEQ ID NO:4)

Using these nested primers, a 511-bp PCR fragment (SEQ ID NO:6) is generated from MBV DNA template.

The experimental designs and findings relating to the development of the PCR method using the two pairs of primers indicated above are illustrated in the following examples:

EXAMPLE 1

Isolation and Purification of MBV Occlusion Bodies from Infected Postlarvae of Tiger Prawns Postlarvae of black tiger prawns suspected to be infected with MBV were randomly examined by staining smeared specimens with eosin to look for occlusion bodies, an indication of MBV infection. Positive MBV-infected postlarvae were frozen and stored on dry ice.

About 500 g of frozen MBV-infected postlarvae were placed in a 1 L beaker and quickly thawed in a 37° C. water bath. They were homogenized with a polytron homogenizer in 20 mM Tris-HCl (pH 7.8) at 4° C. The homogenate was filtered through 300-mesh nylon, and the filtrate was centrifuged at 1,000×g for 10 minutes at 4° C. The pellet was resuspended and emulsified in an organic solvent mixture (20 mM Tris-HCl: n-butanol: n-hexane=10:4:1). After centrifugation again at 2000×g for 20 minutes at 40° C., the pellet was extracted once again with the organic solvent mixture, before being resuspended in Tris buffer, and layered on the top of a 36% to 64% (W/v) continuous sucrose gradient. The gradient was centrifuged at 30,000×g for 1 hour at 18° C., and a white band containing occlusion bodies was collected and suspended in Tris-EDTA buffer (10 mM Tris-HCl, 0.1 mM EDTA). The suspension was centrifuged at 2,500×g for 30 minutes, and the presence of MBV occlusion bodies in the pellet was confirmed by eosin staining. The purified MBV occlusion bodies were stored in Tris-EDTA buffer at −20° C.

The purified occlusion bodies of MBV were stained with eosin and examined under light microscope (FIG. 1). They ranged between 2.5 and 7.5 μm in diameter, which is within the typical size ranges of NPV occlusion bodies.

EXAMPLE 2

Isolation of MBV Genomic DNA

An aliquot of the MBV occlusion body suspension containing 20 μg of protein as determined by Bradford assay was added to 1 ml of TN buffer (10 mM Tris-HCl, pH 8.0, 100 mM NaCl), and digested with proteinase K (100 μg/ml) at 37° C. for 30 minutes. Then, 25 μl of concentrated sodium lauryl sarkosome solution (10%, W/V) and 0.1 volume of 5 M NaCl were added to the reaction mixture in a microfuge tube and mixed on a vortex mixer, which was followed by adding 0.15 volumes of cetyltrimethyl-ammonium bromide (CTAB)/NaCl (10% CTAB in 0.7 M NaCl) with mixing and heating at 65° C. for 30 minutes. The final mixture was extracted once with an equal volume of phenol/chloroform. The supernatant was further extracted twice with an equal volume of phenol/ chloroform/isoamyl alcohol (25:24:1). MBV DNA in the supernatant was then precipitated with 0.6 volumes of isopropanol at room temperature. After centrifugation at 13,000×g for 15 minutes, the MBV DNA pellet was washed with 70% ethanol and dissolved in 10 mM Tris-HCl and 1 mM EDTA, pH 8.0.

The MBV DNA was further examined by PCR using a pair of primers designed from the polyhedrin genes of NPVs. A 674-bp PCR product was generated when the purified MBV DNA was used as template (FIG. 2, Lane 1). Similarly, a 674-bp PCR product was also generated when AcMNPV DNA was used as template (FIG. 2, Lane 2). No PCR product was obtained from WSSV, PMO cells (a cell line derived from the oka organ of Penaeus monodon), or healthy, uninfected hepatopancreatic tissue or intestinal tissue of adult shrimp (FIG. 2, Lanes 3–7). This finding not only confirms the purity of the isolated MBV DNA, but only serves as an indication that using a pair of primers designed from the polyhedrin genes, one can not distinguish MBV from other NPVs (such as AcMNPV) by PCR.

EXAMPLE 3

PCR Amplification Using Primer 1 and Primer 2

Based on the conserved sequences of the DNA polymerase genes of two insect baculoviruses, AcMNPV and LDMNPV, a first pair of primers (Primer 1 and Primer 2, SEQ ID NO:7 and SEQ ID NO:8) was designed, each contained an Xba I recognition site (TCTAGA) at the 5' end. These primers have the DNA sequences of:

Primer 1: 5'-TCTAGAGTIAATCGCGTICACATGCAIA-3' (SEQ ID NO:7)

Primer 2: 5'-TCTAGAATCIATGTGAATGTAITA-3α (SEQ ID NO:8)

PCR amplifications were performed in 100 μl reactions containing 10 ng of viral DNA, 1.6 μM each of the two primers, 10 μl of 10×Dynazyme buffer (purchased from Finnzymes, Espoo, Finland), 20 mM mixture of all four deoxynucleotides, and 5 units of Dynazyme. The reactions were overlaid with mineral oil and heated to 94° C. for 10 minutes before the start of the PCR cycle in a Perkin-Elmer DNA Thermal Cycler (Norwalk, Conn., USA). The first 5 cycling parameters were: denaturing for 2 minutes at 94° C., annealing for 1 minute at 42° C., and extension for 1 minutes at 72° C. This was followed by 30-cycle PCR using the following parameters: denaturing for 2 minutes at 94° C., annealing for 1 minute at 59° C., and extension for 1 minute at 72° C. During the final cycle, extension was for 10 minutes. PCR reactions were stopped at 4° C., and the PCR products were analyzed on a 2% agarose gel. The size of the PCR products was estimated.

The annealing temperature of the first 5 cycles was studied. When the annealing temperature was raised from 42° C. to 45° C., the amount of PCR product obtained was much less (FIG. 3, lane 2). When the annealing temperature raised to 49° C., the PCR product became a smear. Thus, 42° C. was chosen for the annealing temperature of the first 5 PCR cycles.

EXAMPLE 4

BubcloninA & DNA Sequencing of PCR Products Produced by P1 & P2 Primers

Based on the findings as shown in FIG. 4 that the regions where the "I"s (i.e., inosines) in Primer 1 and Primer 2 have changed into "G"s in the 714-bp PCR fragment when MBV DNA is used as template, another first pair of primers, namely, P1 and P2 (SEQ ID NO:1 and SEQ ID NO:2), is designed. P1 and P2 have the following sequences:

P1: 5'-TCTAGAGTGAATCGCGTGCACATGCAGA-3' (SEQ ID NO:1)

P2: 5'-TCTAGAATCGATGTGAATGTAGTA-3' (SEQ ID NO:2)

Using P1 and P2, PCR products were obtained when both MBV and ACMNPV DNA were used as template. MBV produced a 714-bp PCR product (FIG. 5, lane 1). AcMNPV produced a 621-bp PCR product (FIG. 5, lane 2). The results demonstrate that P1 and P2 can be used to detect not only MBV, but also other NPVS.

However, when P1 and P2 were used in other DNA templates, such as WSSV DNA (FIG. 5, lane 3) or DNA of white spot syndrome shrimp, PMO cells (FIG. 5, lane 4), postlarval (FIG. 5, lane 5), hepatopancreatic tissue (FIG. 5, lane 6), or intestinal tissue of adult shrimp (FIG. 5, lane 7), no PCR products were obtained. These findings demonstrate that P1 and P2 are specific for NPVs only. Due to the highly specific property of P1 and P2 to recognize NPV DNA, and to generate different length of PCR products from different NPVs, a PCR method using P1 and P2 to detect MBV has been established.

PCR-amplified DNA was extracted from a 2% agarose gel with an agarose gel extraction kit from Boehringer Mannheim (Germany), digested with Xba I, and ligated to a linearized PGEM 7Zf(−) plasmid. The ligated plasmid (2 μg) was mixed with 0.21 ml of transformation-competent JM109 cells, and the plasmid DNA was transformed into the bacterial host with heat shock at 42° C. for 90 s using standard transformation procedures. Plasmid minipreparations were purified with a Wizard TM DNA cleanup system kit purchased from Promega (Madison, Wis., U.S.A.) before sequencing. DNA sequencing was performed following annealing appropriate primers (20 ng/μl) to alkali-denatured plasmid DNA (5 μg in 8 μl H$_2$O), by an IsoTherm TM sequencing kit.

The 714-bp PCR product generated when MBV DNA was used as template was sequenced (FIG. 4). It contained three TAG stop codons at the 5', end and 2 TAG stop codons at the 3' end (FIG. 4). These five stop codons were always present in the 714-bp PCR products. There was no stop codon in the 465-bp middle region. Sequence comparison (NCBI/BLAST/fasta) between the 714-bp PCR product and the DNA polymerase genes of AcMNPV and LdMNPV revealed that only the primers region of the 714-bp PCR product showed high homology to LDMNPV and AcMNPV, indicating that the 714-bp PCR product was not part of the DNA polymerase gene, but was part of the MBV genomic DNA.

EXAMPLE 5

Detection of MBV Using Primers PA1 and PA2

Two regions within the nucleotide sequence of the 714-bp PCR product (FIG. 4) were selected as forward internal primer PA1 and reverse internal primer PA2 (FIG. 6A):

PA1: 5'-AGTGCTGCAACGACTGGACTGTCC-3' (SEQ ID NO:3)

PA2: 5'-TGATCCTAGGCGTGCCTGTATTGGG-3' (SEQ ID NO:4)

To determine the specificity of PA1 and PA2 for MBV detection, PCR primers based on the sequence of MBV polyhedrin gene (as was used in FIG. 2), P1 and P2 were used for comparative study. Total DNA isolated from shrimp cell line PMO or from various tissues of normal and white-spot-virus-infected penaid shrimp were incubated with different groups of primers and subjected to PCR analysis.

Total DNA from AcMNPV was also tested with PCR primers as described above. PCR products were examined by electrophoresis of samples using 2% agarose gel.

Using PA1 and PA2, only MBV DNA yielded a 511-bp PCR product (FIG. 6B, lane 1). No PCR products were obtained from the DNA templates of ACMNPV, WSSV, PMO, postlarval, hepatopancreatic tissue, or intestinal tissue of tiger prawns (FIG. 6B, lanes 2–7). Because PA1 and PA2 were truly a part of the MBV genome and not a part of the DNA polymerase genes of AcMNPV and LdMNPV, and because PA1 and PA2 did not cross react with the genome from other NPVs (e.g., AcMNPV or LdMNPV), PA1 and PA2 could be used as primers to specifically identify MBV infections in shrimp population.

The second embodiment of the invention provides for an enzyme-linked immunosorbent assay (ELISA) to detect the occlusion bodies of MBV. ELISA is immunological method which uses an enzyme-labeled immunoreactant (antigen or antibody) and an immunosorbent (antigen or antibody bound to a solid) to identify specific serum or tissue antibodies or antigens. The experimental designs and results of this embodiment are illustrated, but not limited to, in the following examples:

EXAMPLE 6

ELISA for Detecting XBV Occlusion Bodies

Polyclonal antibodies against purified occlusion bodies of MBV were produced in a New Zealand rabbit via intraspleenic immunization. The antibodies appeared four weeks after the booster were used for the ELISA test.

The ELISA test was conducted as follows: 0.2 μg of purified occlusion bodies of MBV in 0.05 M sodium carbonate (pH 9.6) were coated onto a 96-well microtiter plate at 4° C. overnight. Then, 3% of bovine serum albumin (BSA) was added to the plate (used as blocking agent) and incubated at 37° C. for 1 hour. The plate was then washed 3 times with buffer. Next, a diluted rabbit anti-MBV serum (1/1000 dilution or different dilutions) was added to the plate and incubated at 37° C. for 1 hour. This was followed by the addition of goat anti-rabbit IgG-horseradish peroxidase serum (1/200 dilution) at 37° C. for 1 hour and 3,3',5,5'-tetramethyl benzidine was added for color development. The color reaction was stopped with 1 N $H_2SO_4$. The optical density of the wells in the microtiter plate was measured at 450 nm with an ELISA reader (Dynatech MR 5000).

For competitive ELISA, rabbit anti-MBV serum was first incubated with competing agent at 37° C. for 1 hour. The mixture was then added to the 96-well microtiter plate pre-coated with MBV occlusion bodies. The rest of the procedures were the same as described above. The optical density obtained in the presence of the competing agent (A) was normalized against the optical density obtained in the absence of the competing antigen ($A_0$).

FIG. 7 is the sensitivity test of the polyclonal antibodies for measuring the occlusion bodies of MBV by ELISA. Both the viral antigen (i.e., the occlusion bodies of MBV) and the polyclonal antibodies were prepared in 10-fold dilution series. The results of this study indicated that the polyclonal antibodies could detect occlusion bodies at nanogram levels.

FIG. 8 is the competitive ELISA test for MBV in which various kinds and amounts of competing agents were pre-incubated with the polyclonal antibodies before the ELISA test. In FIG. 8A, the anti-MBV serum (1/1000 dilution) was pre-incubated with 0, 0.04, 0.08, 0.16, and 0.20 μg of MBV occlusion bodies at 37° C. for 1 hour before adding to the microtiter plate. In FIG. 8B, the MBV antiserum was pre-incubated with various amounts of hepatopancreatic tissue homogenate of tiger prawns Penaeus monodon (P.M.) at 37° C. for 1 hour. In FIG. 8C, various amount of MBV or a fixed amount (40 μg) of the P.M. hepatopancreatic tissue homogenate was first mixed with various amounts of MBV occlusion bodies (0, 0.04, 0.08, 0.16, and 0.20 μg), before pre-incubating with the anti-MBV serum at 37° C. for 1 hour. In FIG. 8D, the anti-MBV serum was pre-incubated with various amounts (10, 20, 30, 40 and 50 μg) of WSSV at 37° C. for 1 hour.

The results of FIG. 8B, C, and D demonstrate that the polyclonal anti-MBV serum was specific to MBV only because it did not cross react with WSSV and the hepatopancreatic tissue homogenate of P.M. The result of FIG. 8C indicates that the competitive ELISA test could detect 0.04 μg of the occlusion bodies of MBV even in 40 μg of P.M. tissue homogenate. These results confirm that the polyclonal antiserum of the occlusion bodies of MBV could be used as a specific diagnostic tool for MBV detection.

It should be understood that the foregoing relates only to preferred specific embodiments of the present invention and that numerous modifications or alterations may be made therein without departing from the spirit and the scope of the invention as set forth in the appended claims.

What is claimed is:

1. A method for detecting a *Penaeus monodon* baculovirus (MBV) comprising:

ampliing DNA in a sample using a pair of primers consisting of the nucleic acid sequences of SEQ ID NO:3 and SEQ ID NO:4 by polymerase chain reaction (PCR) to obtain an amplified product; and analyzing said amplified product by electrophoresis.

2. The method for detecting an MBV according to claim 1, wherein said amplified product is a 511-bp fragment of SEQ ID NO:6.

3. A pair of MBV-specific primers consisting of DNA sequences of SEQ ID NO:3 and SEQ ID NO:4.

* * * * *